United States Patent
Joshi et al.

(10) Patent No.: US 6,491,684 B1
(45) Date of Patent: Dec. 10, 2002

(54) FLUID DELIVERY DEVICE HAVING A WATER GENERATING ELECTROCHEMICAL/CHEMICAL PUMP AND ASSOCIATED METHOD

(75) Inventors: Ashok V. Joshi, Salt Lake City, UT (US); Strahinja K. Zecevic, Salt Lake City, UT (US)

(73) Assignees: Durect Corporation, Cupertino, CA (US); Microlin, L.C., Salt Lake City, UT (US)

( * ) Notice: Subject to any disclaimer, the term of this patent is extended or adjusted under 35 U.S.C. 154(b) by 3 days.

(21) Appl. No.: 09/863,001

(22) Filed: May 22, 2001

(51) Int. Cl.[7] .................................................. A61K 9/22
(52) U.S. Cl. ..................................... 604/892.1; 222/263
(58) Field of Search ................................. 222/263, 389; 604/141, 892.1

(56) References Cited

U.S. PATENT DOCUMENTS

| | | | |
|---|---|---|---|
| 3,995,632 A | * 12/1976 | Nakano et al. | ................ 222/95 |
| 4,552,561 A | 11/1985 | Eckenhoff et al. | |
| 4,717,566 A | * 1/1988 | Eckenhoff et al. | .......... 424/438 |
| 4,734,092 A | 3/1988 | Millerd | |
| 5,062,841 A | * 11/1991 | Siegel | ......................... 424/423 |
| 5,312,389 A | * 5/1994 | Theeuwes et al. | .......... 222/389 |
| 5,312,390 A | * 5/1994 | Wong | .......................... 424/453 |
| 6,287,295 B1 | * 9/2001 | Chen et al. | ............... 604/892.1 |

OTHER PUBLICATIONS

Publication entitled "Handbook of Batteries, Second Edition" at Chapter 13, "Zinc–Air Cells," by Steven R. Bender et al. (available from McGraw–Hill Inc.), pp 13.1–13.20.

* cited by examiner

Primary Examiner—Henry C. Yuen
Assistant Examiner—Melvin Cartagena
(74) Attorney, Agent, or Firm—Factor & Partners, LLC

(57) ABSTRACT

A fluid delivery device generally including: an electrochemical pump, wherein the electrochemical pump is capable of generating water; an electrochemical pump product chamber, wherein the electrochemical pump product chamber is capable of retaining water generated from the electrochemical pump; a displaceable member positioned between the electrochemical pump product chamber and a reservoir, wherein the displaceable member is controllably displaced upon generation of water from the electrical pump; a reservoir, wherein the reservoir is capable of containing a fluid which is delivered upon displacement of the displaceable member; and a housing for containing the electrochemical pump, the electrochemical pump product chamber, the displaceable member, and the reservoir.

29 Claims, 1 Drawing Sheet

FLUID DELIVERY DEVICE HAVING A WATER GENERATING ELECTROCHEMICAL/CHEMICAL PUMP AND ASSOCIATED METHOD

BACKGROUND OF THE INVENTION

1. Field of the Invention

The present invention relates in general to a fluid delivery device, and more particularly, to a fluid delivery device that includes a water generating electrochemical/chemical pump for controllably delivering small volumes of fluid with high precision and accuracy.

2. Background Art

In many situations it is necessary, or, at least, desirable to deliver small amounts of fluids and/or chemical agents over a relatively long period of time. Such fluids may include, among others, medicaments, lubricants, fragrant fluids, and chemical agents. A very common, traditional apparatus for the gradual administration of fluid into the human body is an intravenous administration set in which gravity induced hydrostatic infusion dispenses a fluid from a familiarly suspended bottle or bag above the patient.

Other methods for the gradual administration of fluids have been devised to eliminate the need for suspending the fluid above the patient and thereby provide the patient with greater mobility. Mechanical pump dispensers use various types of mechanical pumps to expel the fluid from a reservoir. Charged reservoir dispensers store a fluid under pressure in a flexible reservoir and then selectively expel that fluid by the force of internal reservoir pressure, the rate of release often being regulated by a plurality of complex valve systems. Pressurized gas dispensers use a pressurized gas to expel the fluid. Osmotic dispensers rely on a solute that exhibits an osmotic pressure gradient against water to dispense the fluid.

While the above-identified fluid administration device types or techniques have become available, there remains a continuing desire for improvements therein. When small quantities of fluids are to be administered continuously over a period of many hours, it is desirable to have a fluid dispenser that is highly accurate and reliable, is sufficiently small and lightweight to be portable, and is convenient and easy to use. Gas generating devices have been developed that are both portable and accurate for dispensing small volumes. These gas-generating methods include galvanic cells and electrolytic cells.

In galvanic gas generating cells, hydrogen or oxygen gas is formed at the cathode or anode, respectively, as a result of a reaction between a metal or metal oxide and an aqueous electrolyte. A galvanic cell is by definition an electrochemical cell that requires no externally applied voltage to drive the electrochemical reactions. Typically, the anode and cathode of the galvanic cell are connected through a resistor that regulates the current passed through the cell, and, in turn, directly regulates the production of gas which exerts a force on a diaphragm or piston—thereby expelling the drug. Joshi et al. have been disclosed a number of delivery systems based on the use of galvanic hydrogen generating cell. Examples of such devices are disclosed in U.S. Pat. Nos. 5,951,538, 5,707,499, and 5,785,688. In the cells disclosed in these patents, a zinc anode react with an alkaline electrolyte producing zinc oxide and water molecules are reduced on porous carbon electrode producing gaseous hydrogen.

U.S. Pat. Nos. 5,242,565 and 5,925,030 disclose a galvanic oxygen-generating cell that is constructed much like a zinc/air button cell battery, where a reducible oxide is reduced at the cathode while hydroxyl ions are formed. Hydroxyl ions oxidize at the anode, releasing oxygen.

In contrast to galvanic cells, an electrolytic cell requires an external DC power source to drive the electrochemical reactions. When voltage is applied to the electrodes, the electrolyte gives off a gas that exerts a force on a diaphragm or piston—thus expelling the drug. Three types of electrolytic gas generating cells have been proposed for use in drug delivery devices. A first type is based on water electrolysis requiring an operating voltage over 1.23 V. A second type, also known as oxygen and hydrogen gas pumps, require lower DC voltage than the water electrolysis systems. Both of these first and second cell types utilize an ion exchanged polymer membrane. A third type of gas generating electrolytic cell is based on the use of an electrolytically decomposable chemical compound that produces a reduced metal at the cathode, and generates gaseous oxygen by oxidation of water at the anode.

U.S. Pat. No. 5,891,097 discloses an electrochemically driven drug dispenser based on electrolysis of water. In this dispenser, water is contained in an electrochemical cell in which porous metal electrodes are joined to both sides of a solid polymer cation exchange membrane, and both the two electrodes are made to contact with water so as to use oxygen or hydrogen generated from an anode or cathode respectively, upon current conduction. Thus, hydrogen, oxygen, or a gas mixture of hydrogen and oxygen, generated by electrolysis of water when a DC current is made to flow between the electrodes, is used as a pressurization source of the drug dispenser.

Electrochemical oxygen and hydrogen pumps are constructed in a similar way to the above discussed water electrolysis cell and are described in several United States patents, including U.S. Pat. Nos. 5,938,640, 4,902,278, 4,886,514, and 4,522,698. Electrochemically driven fluid dispensers disclosed in these patents have an electrochemical cell in which porous gas diffusion electrodes are joined respectively to the opposite surfaces of an ion exchange membrane containing water functioning as an electrolyte. The electrochemically driven fluid dispenser uses such a phenomenon that when hydrogen is supplied to an anode of the electrochemical cell and a DC current is made to flow between the anode and the cathode, the hydrogen becomes hydrogen ions at the anode. When the produced hydrogen ions reach the cathode through the ion exchange membrane, an electrochemical reaction arises to generate gaseous hydrogen thereat. Since the net effect of these processes is transport of hydrogen from one side of the membrane to the other, this cell is also called hydrogen pump. The hydrogen generated and pressurized at the cathode is used as a driving source for pushing a piston, a diaphragm, or the like.

Alternatively, oxygen may be used in place of hydrogen as a reactant in this type of electrochemical cell, wherein the cell then act as an oxygen pump. Thus, oxygen is reduced on one side of a water-containing electrolytic cell and water is oxidized on the opposite side to generate molecular oxygen, with the molecular oxygen so generated being used as the propellant to force liquid from an adjacent reservoir. A variety of different types of devices have been developed and patented.

Gas generating electrolytic cells based on use of electrolytically decomposable chemical compound which produces a reduced metal at the cathode, and generates gaseous oxygen by water oxidation at the anode are disclosed in U.S. Pat. No. 5,744,014. The cell generally includes a graphite anode, an aqueous electrolyte, and a copper hydroxide cathode. As electrical current passes through a circuit in which the cell is connected, copper is plated out in the cathode, and oxygen is released at the anode. To ensure storage stability, an active cathode material is selected such that the cells require an applied voltage for the electrochemical reactions to proceed. A battery is provided in the circuit to drive the current through the gas-generating cell. The rate of oxygen generated at the anode is directly proportional to the current, and acts as a pressurizing agent to perform the work of expelling a fluid from a bladder or other fluid-containing reservoir which has a movable wall which is acted upon as the gas is generated.

While the above-identified electrochemically driven fluid delivery devices are operable for certain applications, they are not optimal for others. In particular, the above-identified fluid delivery devices are based on gas generation, and are suitable for fluid delivery at rates greater than about 20 microliters per day. However, for delivery of very small drug volumes such as about 100 microliters over an extended period of time, and especially for implantable devices, gas generation is not a suitable method for drug delivery. For this purpose, osmotic pumps are more appropriate.

An osmotic pump involves imbibing water or another driving fluid. The pump consists of three chambers: a salt chamber, a water chamber, and a drug chamber. The salt and water chambers are separated by a semi-permeable membrane. This membrane is permeable to water but impermeable to salt. The drug chamber is separated from the other two by a flexible diaphragm. Water imbibes osmotically into the salt chamber creating hydrostatic pressure which, in turn, exerts a force on the diaphragm—thus expelling the drug. The use of osmotic pumps is typically limited to applications requiring constant drug delivery. In order to vary the medicament flow, it is typically necessary to provide numerous osmotic pumps with differing outputs. These limitations make it inconvenient for the patient to use and control such devices. Osmotic pumps also require charging, (the time required for liquid to diffuse through the semi-permeable membrane and begin dissolving the osmagent at steady state) which delays delivery of the medicament, and further limits their suitability for instantaneous or emergency use.

Accordingly, there has been a need for a drug dispenser that is portable, can be miniaturized and therefore implanted, and is highly accurate in the delivering small volumes of fluid with precision and accuracy, that can be programmed at will to change the release rate.

SUMMARY OF THE INVENTION

The present invention is directed to a fluid delivery device, comprising: (a) an electrochemical or chemical pump, wherein the pump is capable of generating water; (b) a pump product chamber, wherein the pump product chamber is capable of retaining water generated from the pump; (c) a displaceable member positioned between the pump product chamber and a reservoir, wherein the displaceable member is controllably displaced upon generation of water from the electrical pump; (d) a reservoir, wherein the reservoir is capable of containing a fluid which is delivered upon displacement of the displaceable member; and (e) a housing for containing the pump, the pump product chamber, the displaceable member, and the reservoir.

In a preferred embodiment of the present invention, the pump comprises a selectively permeable membrane, a wet salt layer, a first electrode, a second electrode, an ion exchange membrane, a DC power source, and an electric resistor. In this embodiment, the pump may further include an activation switch and a support member(s).

In another preferred embodiment of the present invention, the selectively permeable membrane is generally permeable to $H_2O$ molecules, but generally impermeable to $O_2$ molecules, the first and second electrodes are porous gas diffusion electrodes, and/or the ion exchange membrane is a Nafion type membrane.

Preferably, the displaceable member is selected from the group consisting of a piston, bladder, diaphragm, plunger, and mixtures thereof.

In yet another aspect of the present invention, the reservoir includes one or more apertures and contains a fluid selected from the group consisting of a medicament, lubricant, fragrant fluid, chemical agent, and mixtures thereof.

The present invention is also directed to a process for delivering a fluid, comprising the steps of: (a) providing a fluid delivery device having an electrochemical or chemical water generating pump; (b) generating water from the water generating pump; thereby expanding a volume of a pump product chamber; (c) generating pressure from the expanded pump product chamber; and (d) displacing a displaceable member, and, in turn, controllably expelling fluid from the fluid delivery device.

BRIEF DESCRIPTION OF THE DRAWINGS

The invention will now be described with reference to the drawings wherein.

DETAILED DESCRIPTION OF THE INVENTION

Figure 1:
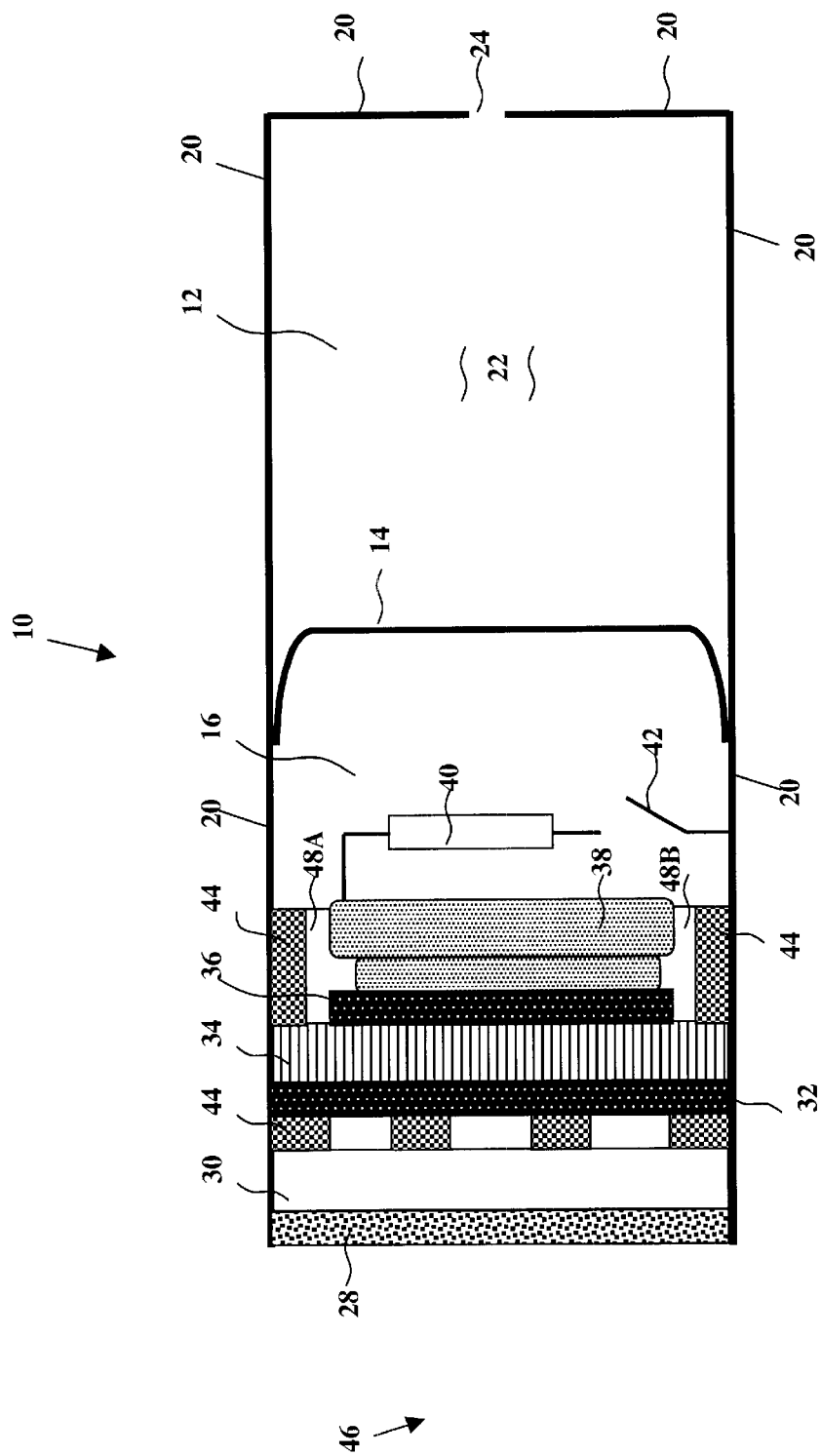
FIG. 1 of the drawings is a cross-sectional schematic representation of a fluid delivery device fabricated in accordance with the present invention.

While this invention is susceptible of embodiment in many different forms, there is shown in the drawings and will herein be described in detail several specific embodiments with the understanding that the present disclosure is to be considered as an exemplification of the principles of the invention and is not intended to limit the invention to the embodiments illustrated.

It will be understood that like or analogous elements and/or components, referred to herein, may be identified throughout the drawings with like reference characters.

Referring now to the drawings and to FIG. 1 in particular, a first embodiment of fluid delivery device 10 is shown, which generally comprises reservoir 12, displaceable member 14, electrochemical pump product chamber 16, electrochemical pump 18, and housing 20. It will be understood that the term "fluid" is herein defined as a liquid, gel, paste, or other semi-solid state material that is capable of being delivered out of a reservoir. It will be further understood that FIG. 1 is merely a schematic representation of fluid delivery device 10. As such, some of the components have been distorted from their actual scale for pictorial clarity.

Reservoir 12 is capable of containing fluid 22, such as a medicament, lubricant, fragrant fluid, chemical agent, or mixtures thereof, which is/are delivered upon displacement of displaceable member 14. Reservoir 12 may include one or more apertures 24 for directing delivery of fluid 22 from fluid delivery device 10. Reservoir 12 may be fabricated from any one of a number of materials, including metals, glass, natural and synthetic plastics, composites—just to name a few.

Displaceable member 14 is positioned between reservoir 12 and electrochemical pump product chamber 16. Displaceable member 14 is shown in FIG. 1, for illustrative purposes only, as comprising a piston, however, other displaceable members that would be known to those having ordinary skill in the art having the present disclosure before them are likewise contemplated for use, including a bladder, diaphragm, plunger, etcetera.

Electrochemical pump product chamber 16 is positioned between displaceable member 14 and electrochemical pump 18, and is capable of containing water that, as will be discussed in greater detail below, is controllably generated during operation of electrochemical pump 18. Similar to reservoir 12, electrochemical pump product chamber 16 may be fabricated from any one of a number of materials, including metals, glass, natural and synthetic plastics, composites—just to name a few.

For purposes of the present disclosure electrochemical pump 18 is shown in FIG. 1 as including selectively permeable membrane 28, wet salt layer 30, first electrode 32, ion exchange membrane 34, second electrode 36, DC power source 38, electric resistor 40, and activation switch 42, and support members 44.

Selectively permeable membrane 28 is positioned at an end of fluid delivery device distal from reservoir 12. Selectively permeable membrane 28 is generally permeable to $H_2O$ molecules, but generally impermeable to $O_2$ molecules, and in cooperation with wet salt layer 30, (e.g. metal halides, such as NaCl) which emanates contiguously therefrom, enables water from external source 46 (e.g. an inside of a living being's body) to osmotically diffuse or migrate toward first electrode 32. Typical compositions comprising selectively permeable membrane 28 are known in the art, a non inclusive list includes the group consisting of a cellulose ester, a cellulose ether and a cellulose ester-ether, including, for example, cellulose acetate butyrate. They are commercially available from Himont.

First electrode 32, ion exchange member 34, and second electrode 36 are respectively positioned adjacent wet salt layer 30. First and second electrodes 32 and 36 are porous and preferably gas diffusion electrodes with a platinum catalyst supported on high surface area carbon, or, alternatively they can be in the form of a thin porous metal-ink type coating. Although not shown, first and second electrodes may include conventional current collectors, such as screen or mesh current collectors fabricated from, for example, titanium, nickel, platinum, or other corrosion stable metals. While specific examples of electrode materials have been disclosed, for illustrative purposes, it will be understood that other electrode materials known to those with ordinary skill in the art having the present disclosure before them are likewise contemplated for use.

Ion exchange membrane 34 is positioned between first electrode 32 and second electrode 36, and is preferably a perfluorinated type membrane such as Nafion, for example, which is commercially available from DuPont. The function of ion exchange membrane 34 will be discussed in detail below.

Power source 38 emanates contiguously from second electrode 36 and is preferably fabricated from a lithium, silver, or other high-energy cell, such as a button cell.

Electric resistor 40 is connected to power source 38 via conventional electrical conduit and, as will be discussed in greater detail below, directly controls the rate of water transfer from external source 46 to electrical pump product chamber 16.

Support members 44 are highly porous solid disk materials, that provide mechanical rigidity for the electrolytic membrane cell, and allow water to transport through it. They can be made of hard plastics or corrosion stable metals (e.g. titanium), or a combination thereof.

In operation, fluid delivery device 10 can deliver fluid 22 in accordance with the following process. Initially, activation switch 42 is actuated, whereupon an electrical circuit is complete and a voltage is applied from power source 38 across second and first electrodes 36 and 32, which causes an electrode reaction to take place and water to be extracted from external environment 46, and, ultimately to be driven across ion exchange membrane 34 into electrical pump product chamber 16. Thus, water from external environment, such as a human body diffuses by osmotic action through selectively permeable membrane 28 and wet salt (NaCl) layer 30 to first electrode 32. The selectively permeable membrane 28 is generally permeable to $H_2O$ molecules and generally impermeable to $O_2$ molecules. At first electrode 32, water molecules take part in an electrode oxidation reaction producing $O_2$ and $H^+$ according to the equation:

$$2H_2O \rightarrow O_2 + 4H^+ + 4e^- \qquad (1)$$

Oxygen molecules and hydrogen ions thus formed are dissolved in water and travel through ion exchange membrane 34 toward second electrode 36. Oxygen molecules are also dissolved in the ion exchange membrane, as it taught Zecevic et al., "Kinetics of $O_2$ reduction on a Pt electrode covered with a thin film of solid polymer electrolyte", *J. Electrochem. Soc.*, 144 (1997) 2973–2982. Oxygen molecules travel by diffusion (under the influence of the $O_2$ concentration gradient) whereas hydrogen ions travel by migration (under the influence of the electric field). At second electrode 36 they react undergoing a reduction, which produces water according to the equation:

$$O_2 + 4H^+ + 4e^- \rightarrow 2H_2O \qquad (2)$$

In addition to the electrochemical formation of water according to equation (2), during passage of the hydrogen ions through the membrane, water is entrained with ions so that at the opposite side of the membrane additional amount of water is produced. Water molecules thus formed go through apertures 48A and 48B between support members 44 and power source 38.

The formed water molecules enter electrochemical pump product chamber 16 and generate pressure within the electrochemical pump product chamber 16. The generated pressure, in turn, imparts a force upon displaceable member 14—the only movable component. Displaceable member 14 is displaced laterally away from electrochemical pump product chamber 16, which controllably expels fluid from reservoir 12. It will be understood that the above-identified device and process enables a controlled delivery of a fluid over an extended period of time at a relatively precise and accurate rate inasmuch as the water formed is proportional to the current, which in turn depends on the value of resistor 48. It will be understood, therefore, that the fluid delivery rate is controlled by selection of the resistor and not by the rate at which water is permitted to enter the housing via osmotic action of selectively permeable membrane 28.

The foregoing description merely explains and illustrates the invention and the invention is not limited thereto except insofar as the appended claims are so limited, as those skilled in the art who have the disclosure before them will be able to make modifications without departing the scope of the invention.

What is claimed is:

1. A fluid delivery device, comprising:
an electrochemical pump, wherein the electrochemical pump is capable of generating water;
an electrochemical pump product chamber, wherein the electrochemical pump product chamber is capable of retaining water generated from the electrochemical pump;
a displaceable member positioned between the electrochemical pump product chamber and a reservoir, wherein the displaceable member is controllably displaced upon generation of water from the electrochemical pump;
a reservoir, wherein the reservoir is capable of containing a fluid which is delivered upon displacement of the displaceable member; and
a housing for containing the electrochemical pump, the electrochemical pump product chamber, the displaceable member, and the reservoir.

2. The fluid delivery device according to claim 1, wherein the electrochemical pump comprises a selectively permeable membrane, a wet salt layer, a first electrode, a second electrode, an ion exchange membrane, a DC power source, and an electric resistor.

3. The fluid delivery device according to claim 2, wherein the electrochemical pump further includes an activation switch, and a support member.

4. The fluid delivery device according to claim 2, wherein the selectively permeable membrane is generally permeable to $H_2O$ molecules, but generally impermeable to $O_2$ molecules.

5. The fluid delivery device according to claim 2, wherein the first and second electrodes are porous gas diffusion electrodes.

6. The fluid delivery device according to claim 2, wherein the ion exchange membrane is a perfluorinated type membrane.

7. The fluid delivery device according to claim 2, wherein the DC power source is a button cell.

8. The fluid delivery device according to claim 1, wherein the displaceable member is selected from the group consisting of a piston, bladder, diaphragm, plunger, and mixtures thereof.

9. The fluid delivery device according to claim 1, wherein the reservoir contains a fluid selected from the group consisting of a medicament, lubricant, fragrant fluid, chemical agent, and mixtures thereof.

10. The fluid delivery device according to claim 1, wherein the reservoir includes one or more apertures.

11. A fluid delivery device, comprising:
an electrochemical pump, wherein the electrochemical pump is capable of generating water, and wherein the electrochemical pump includes a selectively permeable membrane, a wet salt layer, a first electrode, a second electrode, an ion exchange membrane, a DC power source, and an electric resistor;
an electrochemical pump product chamber, wherein the electrochemical pump product chamber is capable of retaining water generated from the electrochemical pump;
a displaceable member positioned between the electrochemical pump product chamber and a reservoir, wherein the displaceable member is controllably displaced upon generation of water from the electrochemical pump;
a reservoir, wherein the reservoir is capable of containing a fluid which is delivered upon displacement of the displaceable member; and
a housing for containing the electrochemical pump, the electrochemical pump product chamber, the displaceable member, and the reservoir.

12. The fluid delivery device according to claim 11, wherein the electrochemical pump further includes an activation switch, and a support member.

13. The fluid delivery device according to claim 11, wherein the selectively permeable membrane is generally permeable to $H_2O$ molecules, but generally impermeable to $O_2$ molecules.

14. The fluid delivery device according to claim 11, wherein the first and second electrodes are porous gas diffusion electrodes.

15. The fluid delivery device according to claim 11, wherein the ion exchange membrane is a perfluorinated type membrane.

16. The fluid delivery device according to claim 11, wherein the DC power source is a button cell.

17. The fluid delivery device according to claim 11, wherein the displaceable member is selected from the group consisting of a piston, bladder, diaphragm, plunger, and mixtures thereof.

18. The fluid delivery device according to claim 11, wherein the reservoir contains a fluid selected from the group consisting of a medicament, lubricant, fragrant fluid, chemical agent, and mixtures thereof.

19. The fluid delivery device according to claim 11, wherein the reservoir includes one or more apertures.

20. A fluid delivery device, comprising:
an electrochemical pump, wherein the electrochemical pump is capable of generating water, and wherein the electrochemical pump includes:
a selectively permeable membrane positioned at an end of the fluid delivery device;
a wet salt layer which emanates contiguously from the selectively permeable membrane;
a first electrode which emanates contiguously from the wet salt layer;
an ion exchange membrane which emanates contiguously from the first electrode;
a second electrode which emanates contiguously from the ion exchange membrane;
a button cell which emanates contiguously from the second electrode; and
an electric resistor which is in electrical communication with the button cell;
an electrochemical pump product chamber, wherein the electrochemical pump product chamber is capable of retaining water generated from the electrochemical pump;
a displaceable member positioned between the electrochemical pump product chamber and a reservoir, wherein the displaceable member is controllably displaced upon generation of water from the electrical pump;
a reservoir, wherein the reservoir is capable of containing a fluid which is delivered upon displacement of the displaceable member; and
a housing for containing the electrochemical pump, the electrochemical pump product chamber, the displaceable member, and the reservoir.

21. The fluid delivery device according to claim 20, wherein the electrochemical pump further includes an activation switch, and a support member.

22. The fluid delivery device according to claim 20, wherein the selectively permeable membrane is generally permeable to $H_2O$ molecules, but generally impermeable to $O_2$ molecules.

23. The fluid delivery device according to claim 20, wherein the first and second electrodes are porous gas diffusion electrodes.

24. The fluid delivery device according to claim 20, wherein the ion exchange membrane is a perfluorinated type membrane.

25. The fluid delivery device according to claim 20, wherein the button cell is a lithium, silver, or other metal, high-energy cell.

26. The fluid delivery device according to claim 20, wherein the displaceable member is selected from the group consisting of a piston, bladder, diaphragm, plunger, and mixtures thereof.

27. The fluid delivery device according to claim 20, wherein the reservoir contains a fluid selected from the group consisting of a medicament, lubricant, fragrant fluid, chemical agent, and mixtures thereof.

28. The fluid delivery device according to claim 20, wherein the reservoir includes one or more apertures.

29. A process for delivery a fluid, comprising the steps of:

providing a fluid delivery device having an electrochemical water-generating pump;

generating water from the electrochemical water generating pump; thereby expanding a volume of an electrochemical pump product chamber;

generating pressure from the expanded electrochemical pump product chamber; and displacing a displaceable member, and, in turn, controllably expelling fluid from the fluid delivery device.

* * * * *